(12) United States Patent
Dakka et al.

(10) Patent No.: US 7,326,815 B2
(45) Date of Patent: Feb. 5, 2008

(54) SELECTIVE OXIDATION OF ALKYLBENZENES

(75) Inventors: Jihad Mohammed Dakka, Whitehouse Station, NJ (US); Doron Levin, Annandale, NJ (US); Jon Edmond Randolph Stanat, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/318,731

(22) Filed: Dec. 27, 2005

(65) Prior Publication Data

US 2007/0265476 A1    Nov. 15, 2007

(51) Int. Cl.
C07C 45/53 (2006.01)
C07C 37/08 (2006.01)

(52) U.S. Cl. ...................... 568/385; 568/768
(58) Field of Classification Search ............... None
See application file for complete search history.

(56) References Cited

U.S. PATENT DOCUMENTS

| | | | |
|---|---|---|---|
| 4,490,565 A | 12/1984 | Chang et al. | 568/798 |
| 4,490,566 A | 12/1984 | Chang et al. | 568/798 |
| 4,992,606 A | 2/1991 | Kushnerick et al. | 585/467 |
| 5,183,945 A | 2/1993 | Stibrany et al. | 568/574 |
| 5,298,667 A | 3/1994 | Iwanaga et al. | 568/385 |
| 5,334,774 A | 8/1994 | Kogure et al. | 568/754 |
| 5,336,820 A | 8/1994 | Owen et al. | 582/323 |
| 5,922,920 A | 7/1999 | Bond et al. | 568/342 |
| 6,002,057 A | 12/1999 | Hendriksen et al. | 585/448 |
| 6,051,521 A | 4/2000 | Cheng et al. | 502/86 |
| 6,169,215 B1 | 1/2001 | Levin et al. | 568/798 |
| 6,169,216 B1 | 1/2001 | Levin et al. | 568/798 |
| 6,297,406 B1 | 10/2001 | Levin et al. | 568/798 |
| 6,410,804 B1 | 6/2002 | Levin et al. | 568/798 |
| 6,440,886 B1 | 8/2002 | Gajda et al. | 502/64 |
| 6,476,276 B2 | 11/2002 | Matsui et al. | 568/569 |
| 6,720,462 B2 | 4/2004 | Kuhnle et al. | 568/768 |
| 6,852,893 B2 | 2/2005 | Kühnle et al. | 568/314 |
| 2002/0026680 A1 | 3/2002 | Kingry et al. | 15/228 |
| 2003/0083527 A1 | 5/2003 | Kühnle et al. | 568/382 |
| 2004/0162448 A1 | 8/2004 | Yang et al. | 568/577 |
| 2004/0236152 A1 | 11/2004 | Black et al. | 568/414 |

FOREIGN PATENT DOCUMENTS

| | | |
|---|---|---|
| EP | 0 548 986 | 6/1993 |
| EP | 0 578 194 | 12/1994 |
| EP | 0 824 962 | 2/1998 |
| EP | 0 858 835 | 8/1998 |
| EP | 1 088 809 | 8/2000 |
| FR | 2 182 802 | 12/1973 |
| JP | 2002-282698 | 10/2002 |
| JP | 2003-34679 | 2/2003 |

OTHER PUBLICATIONS

Process Economics Report No. 23B entitled "Phenol" published by the Stanford Research Institute in Dec. 1977, pp. 261-263.
Ishii et al., *J. Org. Chem.* 1995, 60, 3934-3935.
Burghardt et al., *Chemia Stosowana* 1979, XXIII, 4, 443-458.
Sheldon et al., *Adv. Synth. Catal.* 2004, 346, 1051-1071.
Process Economics Report No. 22B entitled"Phenol" published by the Stanford Research Institute in Dec. 1977, pp. 113-244.
U.S. Appl. No. 60/601,661, filed Aug. 8, 2004, Cheng et al.

*Primary Examiner*—Sikarl A. Witherspoon
(74) *Attorney, Agent, or Firm*—Andrew B. Griffis

(57) ABSTRACT

The present invention relates to a process for producing phenol and a ketone of general formula $R^1COCH_2R^3$ (I), in which $R^1$ and $R^2$ each independently represent an alkyl group having from 1 to 4 carbon atoms, said process comprising:

(a) providing an alkylbenzene feedstock comprising
  (i) an alkylbenzene of general formula (II)

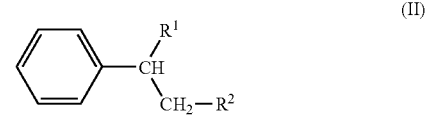

in which $R^1$ and $R^2$ have the same meaning as in formula (I) and
(ii) at least one structural isomer of said alkylbenzene of formula (II) in an amount of at least 0.7% of the weight of alkylbenzene of formula (II),
(b) submitting the alkylbenzene feedstock to oxidation conditions in the presence of oxygen and in the presence of a cyclic imide of formula (III):

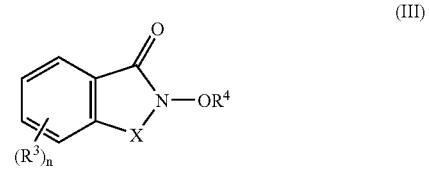

in which X represents a carbonyl (CO) group or a sulfonyl ($SO_2$) group, n is 0, 1, 2, 3 or 4, $R^3$ is one or several groups selected from a hydrogen atom, a halogen atom, an alkyl group, an alkoxy group, an amino group and $R^4$ is a hydrogen atom, an alkaline metal cation or an alkaline earth metal cation, or in the presence of N,N',N"-trihydroxyisocyanuric acid (THICA), to produce a product comprising a hydroperoxide of general formula (IV)

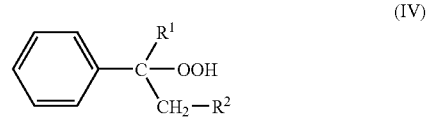

in which $R^1$ and $R^2$ have the same meaning as in formula (I), and
(c) converting the hydroperoxide of formula (IV) into phenol and a ketone of formula (I).

36 Claims, 9 Drawing Sheets

SELECTIVE OXIDATION OF ALKYLBENZENES

FIELD OF THE INVENTION

The present invention relates to a process for producing phenol and a ketone of general formula $R^1COCH_2R^2$ (I), in which $R^1$ and $R^2$ each independently represent an alkyl group having from 1 to 4 carbon atoms, from an alkylbenzene feedstock.

BACKGROUND OF THE INVENTION

Phenol and ketones of general formula $R^1COCH_2R^2$ (I), in which $R^1$ and $R^2$ each independently represent an alkyl group having from 1 to 4 carbon atoms, such as methyl ethyl ketone, are important products in the chemical industry. For example, phenol is useful in the production of phenolic resins, bisphenol A, ε-caprolactam, adipic acid, alkyl phenols, and plasticizers, and methyl ethyl ketone is widely used as a lacquer, a solvent and for dewaxing of lubricating oils.

A common route for the production of methyl ethyl ketone (MEK) is by dehydrogenation of sec-butyl alcohol (SBA), with the alcohol being produced by the acid-catalyzed hydration of butenes. Commercial scale SBA manufacture by hydration of butylene with sulfuric acid has been accomplished for many years via gas absorption/liquid extraction. Improvements to this hydration process include a process configuration that utilizes a unique combination of plug flow, bubble column, and CSTR (Stirred Tank Reactor) reaction sections to achieve high conversion of butylene. Other improved processes use spargers, custom-designed for butylene/sulfuric acid absorption/extraction. Also, loop reactors may be preferred to improve mixing intensity. In sec-butyl alcohol dehydrogenation, crude sec-butyl alcohol is recovered in absorption or extraction sections using several towers, preferably, a single tower, to separate sec-butyl alcohol from sec-butyl ether.

Currently, the most common route for the production of phenol is the Hock process. This is a three-step process in which the first step involves alkylation of benzene with propylene to produce cumene, followed by oxidation of cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that for butenes is likely to increase, due to a developing shortage of propylene. Thus, a process that uses butenes or higher alkenes instead of propylene as feed and co-produces MEK or higher ketones rather than acetone may be an attractive alternative route of the production to phenol.

It is known that phenol and MEK can be produced from sec-butylbenzene by the Hock process, where sec-butylbenzene (SBB) is oxidized to obtain sec-butylbenzene hydroperoxide (SBBHP) and the peroxide is decomposed to the desired phenol and methyl ethyl ketone. An overview of such a process is described in pages 113-244 and 261-263 of Process Economics Report no. 22B entitled "Phenol", published by the Stanford Research Institute in December 1977.

Methods for making phenol and MEK or higher ketones by oxidation of alkylbenzenes have also been described in several other documents.

U.S. Pat. No. 5,298,667 and EP-A-548,986 disclose a process for producing phenol and MEK which comprises the steps of (I) oxidizing one material selected from (A) sec-butylbenzene substantially free from ethyl hydroperoxide, carboxylic acids and phenol, (B) sec-butylbenzene substantially free from styrenes, and (C) sec-butylbenzene substantially free from methylbenzyl alcohol, to obtain sec-butylbenzene hydroperoxide, with an oxygen-containing gas and in the absence of a catalyst, and (II) decomposing the sec-butylbenzene hydroperoxide to obtain phenol and MEK with an acidic catalyst.

EP-A-1,088,809 discloses a process for producing phenol, MEK and acetone by the oxidation of a mixture containing cumene and up to 25 wt % sec-butylbenzene and the subsequent Hock cleavage of the hydroperoxides, so that the ratio of the phenol:acetone:MEK in the product can be controlled via the composition of the feed mixture. The feed mixture is produced directly by the alkylation of benzene with a corresponding mixture of propene and 1-butene/2-butene in the presence of a commercial alkylation catalyst such as $AlCl_3$, $H_3PO_4/SiO_2$ or a zeolite. Oxidation takes place in the presence of air or oxygen and in the absence of a catalyst.

FR-A-2,182,802 discloses a process for producing phenol and MEK by oxidation of sec-butylbenzene, in which sec-butylbenzene is oxidized to sec-butylbenzene hydroperoxide in the presence of air and optionally in the presence of sec-butylbenzene hydroperoxide, followed by peroxide decomposition. According to this document, sec-butylbenzene must not contain more than 1 wt. % isobutylbenzene, as isobutylbenzene significantly affects the overall process efficiency and yield in phenol and methyl ethyl ketone.

U.S. 2004/0162448 and U.S. 2004/0236152 disclose processes for producing phenol and acetone and/or MEK, in which a mixture of cumene and sec-butylbenzene is oxidized to the corresponding peroxides in the presence of oxygen, followed by peroxide decomposition. The oxidation mixture may also contain cumene hydroperoxide as initiator, but does not contain any catalyst. According to these documents, the addition of a neutralizing base in the oxidation mixture improves the yield in hydroperoxide and reduces the formation of undesired side products.

U.S. Pat. No. 6,852,893 and U.S. Pat. No. 6,720,462 describe methods for producing phenol by catalytic oxidation of alkyl aromatic hydrocarbons to the corresponding hydroperoxide, and subsequent cleavage of the hydroperoxide to give phenol and a ketone. Catalytic oxidation takes place with oxygen, in the presence of a free radical initiator and a catalyst, typically an N-hydroxycarbodiimide catalyst, such as N-hydroxyphthalimide. Preferred substrates that may be oxidized by this process include cumene, cyclohexylbenzne, cyclododecylbenzene and sec-butylbenzene.

Oxydation of alkylbenzenes with N-hydroxyphthalimide is also mentioned in Y. Ishii et al., *J. Org. Chem.* 1995, 60, 3934-3935; EP-A1-858835; EP-A1-824962; U.S. Pat. No. 6,476,276 and JP-A-2003-034679 as well as in A. Burghardt et al., *Chemia Stosowana* 1979, XXIII, 4, 443-458, and in R. A. Sheldon et al., *Adv. Synth. Catal.* 2004, 346, 1051-1071.

In comparison to cumene, oxidation of aromatic compounds substituted by branched alkyl groups having 4 or more carbon atoms, such as sec-butylbenzene, to the corresponding hydroperoxide requires higher temperatures and is very sensitive to the presence of impurities. For example, at about 110° C. cumene easily undergoes atmospheric air oxidation, while sec-butylbenzene does not undergo any significant oxidation. Atmospheric air oxidation of sec-butylbenzene requires higher temperatures than cumene oxidation, with the inconvenience that higher temperatures lead to poor selectivity to the desired phenol and ketone products.

Without wishing to be bound by any theory, it is believed that branched alkyl substituents on the benzene ring, having 4 or more carbon atoms, can undergo carbon-carbon bond scission at the beta position from the benzene ring under oxidation conditions, thereby generating alkyl radicals that terminate radical chain propagation and preventing oxidation to take place.

Furthermore, certain by-products formed during alkylbenzene manufacture typically present in alkylbenzenes where the alkyl group has 4 carbon atoms or more also inhibit alkylbenzene oxidation.

These drawbacks have, up to now, limited the use of the Hock reaction to make phenol from alkylbenzenes in which the alkyl chain has 4 or more carbon atoms. There thus remains a need to find new alkylbenzene oxidation conditions that are much less sensitive to the presence of impurities than the existing oxidation processes, and that allow selective and efficient commercial scale production of phenol and ketones of formula (I) by the Hock process.

SUMMARY OF THE INVENTION

The present invention is directed to a process for producing phenol and a ketone of general formula $R^1COCH_2R^2$ (I), in which $R^1$ and $R^2$ each independently represent an alkyl group having from 1 to 4 carbon atoms, said process comprising:

(a) providing an alkylbenzene feedstock comprising (i) an alkylbenzene of general formula (II)

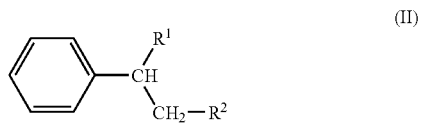

(II)

in which $R^1$ and $R^2$ have the same meaning as in formula (I) and (ii) at least one structural isomer of said alkylbenzene of formula (II) in an amount of at least 0.7%, preferably at least 1.0%, more preferably at least 1.5% of the weight of alkylbenzene of formula (II), (b) submitting the alkylbenzene feedstock to oxidation conditions in the presence of oxygen and in the presence of a cyclic imide of formula (III):

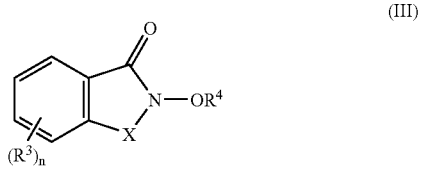

(III)

in which X represents a carbonyl (CO) group or a sulfonyl ($SO_2$) group n is 0, 1, 2, 3 or 4, $R^3$ is one or several groups selected from a hydrogen atom, a halogen atom, an alkyl group, an alkoxy group, an amino group and $R^4$ is a hydrogen atom, an alkaline metal cation or an alkaline earth metal cation, or in the presence of N,N',N"-trihydroxyisocyanuric acid (THICA) to produce a product comprising a hydroperoxide of general formula (IV)

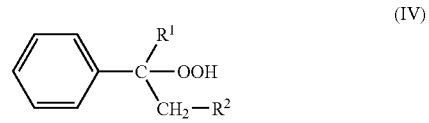

(IV)

in which $R^1$ and $R^2$ have the same meaning as in formula (I), and (c) converting the hydroperoxide of formal (IV) into phenol and a ketone of formula (I).

Suitable conditions for oxidation step include a temperature between about 70° C. and about 200° C., such as between about 90° C. to about 130° C., preferably between 100° C. to about 125° C., and more preferably between 105° C. to about 120° C. and a pressure of from about 50 to 1000 kPa (0.5 to about 10 atmospheres), preferably of from about 50 kPa to 500 kPa (0.5 to 5 atmospheres), and more preferably of from about 90 kPa to 150 kPa (0.9 to 1.5 atmospheres).

Most preferably, R1 and R2 represent a methyl group.

DETAILED DESCRIPTION

Figure 1:
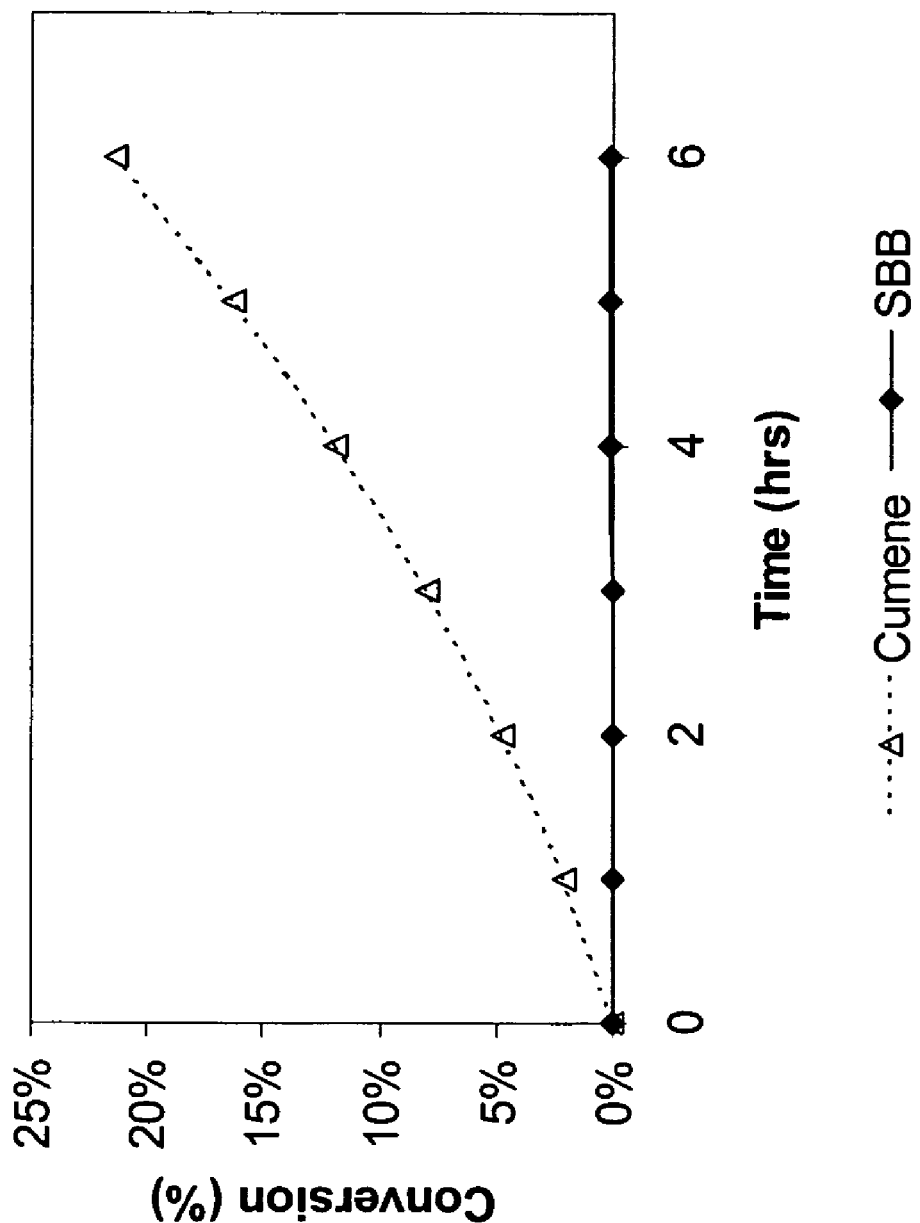
FIG. 1 shows cumene and SBB conversion during oxidation with air under atmospheric pressure at 110° C.

The present invention is directed to a process for producing phenol and a ketone of general formula $R^1COCH_2R^2$ (I), in which $R^1$ and $R^2$ each independently represent an alkyl group having from 1 to 4 carbon atoms, said process comprising:

(a) providing an alkylbenzene feedstock comprising (i) an alkylbenzene of general formula (II)

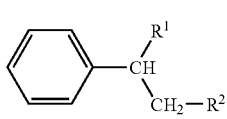
(II)

in which $R^1$ and $R^2$ have the same meaning as in formula (I) and (ii) at least one structural isomer of said alkylbenzene of formula (II) in an amount of at least 0.7% of the weight of alkylbenzene of formula (II), (b) submitting the alkylbenzene feedstock to oxidation conditions in the presence of oxygen and in the presence of a cyclic imide of formula (III):

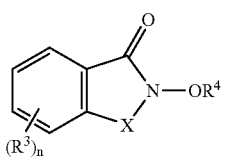
(III)

in which X represents a carbonyl (CO) group or a sulfonyl ($SO_2$) group n is 0, 1, 2, 3 or 4, $R^3$ is one or several groups selected from a hydrogen atom, a halogen atom, an alkyl group, an alkoxy group, an amino group and $R^4$ is a hydrogen atom, an alkaline metal cation or an alkaline earth metal cation, or in the presence of N,N',N''-trihydroxyisocyanuric acid (THICA) to produce a product comprising a hydroperoxide of general formula (IV)

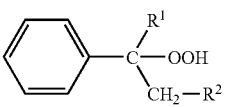
(IV)

in which $R^1$ and $R^2$ have the same meaning as in formula (I), and (c) converting the hydroperoxide of formula (IV) into phenol and a ketone of formula (I).

In particular, the invention is based on the fact that the aforementioned alkylbenzene feedstock can easily and conventionally undergo oxidation to phenol and a ketone of formula (I), despite the presence of structural isomeric impurities in the alkylbenzene feedstock. The presence of a cyclic imide of formula (III) in the reaction mixture, optionally coupled with a particular selection of oxidation conditions, unexpectedly suppresses the inhibiting effect of the structural isomeric impurities during oxidation.

The Alkylbenzene Feedstock

The alkylbenzene feedstock used in this invention is a feedstock comprising an alkylbenzene of general formula (II)

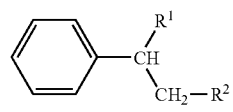
(II)

in which $R^1$ and $R^2$ independently represent an alkyl group having from 1 to 4 carbon atoms, such as a methyl group, an ethyl group, a 1-propyl group, a 2-propyl group, a 1-butyl group, a 2-butyl group, an isobutyl group or a tertbutyl group. Preferably, $R^1$ and $R^2$ independently represent a methyl group or an ethyl group. Most preferably, $R^1$ and $R^2$ both represent a methyl group, i.e. the alkylbenzene of formula (II) is sec-butylbenzene.

Preferably, the alkylbenzene of formula (II), conveniently sec-butylbenzene, represents at least 80 wt. % of the alkylbenzene feedstock, more preferably at least 90 wt % of the alkylbenzene feedstock, even more preferably at least 95 wt % of the alkylbenzene feedstock, and most preferably at least 97 wt % of the alkylbenzene feedstock.

The alkylbenzene feedstock used in the present invention also contains at least one structural isomer of the alkylbenzene of formula (II). In the context of this invention, a structural isomer of the alkylbenzene of formula (II) is a monoalkylbenzene, in which the alkyl side chain has the same number of carbon atoms as the alkyl side chain of the alkylbenzene of formula (II), but the alkyl side chain of the structural isomer has a different connectivity than the carbon atoms of the alkyl side chain of the alkylbenzene of formula (II). For example, structural isomers of sec-butylbenzene include one or several of iso-butylbenzene, tert-butylbenzene, 4-phenyl-1-butene or 2-methyl-1-phenylpropene.

Alkylbenzene feedstocks used in the invention are available commercially in large industrial scales. Such feedstocks are typically manufactured by alkylation of benzene with alkene feedstreams, in the presence of a catalyst. For example, the conventional route for the production of sec-butylbenzene involves contacting benzene with an n-butene feedstream in the presence of a homogeneous catalyst, such as $AlCl_3$, or in the presence of a heterogeneous catalyst, such as solid phosphoric acid or a zeolite, for example, MCM-22, PSH-3, SSZ-25, ITQ-1, ITQ-2, MCM-36, MCM-49, MCM-56, UZM-8. The product of alkylation is a sec-butylbenzene (SBB) product typically containing n-butylbenzene (NBB), isobutylbenzene (IBB), tert-butylbenzene (tBB), dibutylbenzenes (DBB), and tributylbenzenes (TBB) as by-products. The amounts of by-products generated depend on several factors, including the presence of butene isomers in the n-butene feedstream, the severity of the alkylation conditions, and the selectivity of the alkylation catalyst.

Polyalkylbenzenes that form during benzene alkylation can be separated from the desired monoalkylbenzene by methods known in the art, such as distillation. However, structural isomers of the desired alkylbenzene of formula (II) typically have very close physical properties (f. ex. boiling points), making their separation from the desired alkylbenzene of formula (II) extremely difficult.

The present invention allows to perform oxidation of alkylbenzene feedstock contain residual amounts of structural isomers in the alkylbenzene feedstock. Accordingly, structural isomers of the alkylbenzene of formula (II) are present in the alkylbenzene feedstock in an amount of at least 0.7%, preferably at least 1.0%, more preferably at least 1.5%, of the weight of the alkylbenzene of formula (II).

Conveniently, the amount of structural isomer present in the alkylbenzene feedstock does not exceed 10%, preferably does not exceed 5%, more preferably does not exceed 4% and even more preferably does not exceed 3% of the weight of the predominant alkylbenzene of formula (II).

Optionally, the alkylbenzene feedstock may also contain cumene, in an amount that does not exceed 10%, preferably that does not exceed 8%, and more preferably that does not exceed 5%, of the weight of alkylbenzene of formula (II).

Alkylbenzene Feedstock Oxidation

The process of the invention oxidizes the alkylbenzene feedstock to the corresponding hydroperoxide of formula

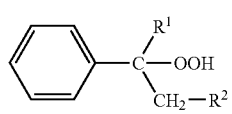

(IV)

in which $R^1$ and $R^2$ have the same meaning as in formula (I). This oxidation process can take place in one or more oxidation reactor(s). The oxidation reactor(s) may be batch reactor(s) or continuous reactor(s).

The alkylbenzene feedstock is oxidized in the presence of an oxygen-containing gas, such as air. While a solvent may be added to the alkylbenzene feedstock, oxidation is typically carried out in the absence of any solvent, other than the alkylbenzene feedstock itself.

Alkylbenzene feedstock oxidation also takes place in the presence of at least one substituted cyclic imide of formula

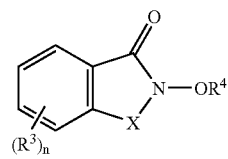

(III)

in which X represents a carbonyl (CO) group or a sulfonyl ($SO_2$) group, n is 0, 1, 2, 3 or 4, $R^3$ is one or several groups selected from a hydrogen atom, a halogen atom, an alkyl group, an alkoxy group, an amino group and $R^4$ is a hydrogen atom, an alkaline metal cation or an alkaline earth metal cation. Preferably, the cyclic imide of formula (III) is selected from the group consisting of N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxysaccharin and mixtures thereof. Most preferably, the cyclic imide of formula (III) is N-hydroxyphthalimide, hereinafter abbreviated NHPI.

Alternatively alkylbenzene feedback oxidation takes place in the presence of N,N',N"-trihydroxyisocyanuric acid (THICA).

Preferably, the cyclic imide of formula (III) or THICA is used in an amount of from 0.0001 mol % to 15 mol %, preferably from 0.001 mol % to 10 mol %, relative to the amount of alkylbenzene of formula (II).

In a separate embodiment, the cyclic imide of formula (III) or THICA is used in a form in which it has been deposited or fixed chemically on a support, for example, silica, alumina, a zeolite, a polymer (e.g. polystyrene resin) or a mixture thereof.

The oxidation mixture may also optionally comprise a free radical initiator, such as a peroxy compound or azo compound. Examples of such compounds are cumene hydroperoxide and sec-butylbenzene hydroperoxide. If used, the free radical initiator is usually present in an amount that is less than the amount of cyclic imide of formula (III).

Suitable conditions for oxidation step include a temperature between about 70° C. and about 200° C., such as between about 90° C. to about 130° C., preferably between 100° C. to about 125° C., and more preferably between 105° C. to about 120° C. and a pressure of from about 50 to 1000 kPa (0.5 to about 10 atmospheres), preferably of from about 50 kPa to 500 kPa (0.5 to 5 atmospheres), and more preferably of from about 90 kPa to 150 kPa (0.9 to 1.5 atmospheres).

A basic agent, such as an alkali metal carbonate (f. ex. sodium carbonate), an alkali metal bicarbonate (f. ex. sodium bicarbonate), or ammonia may also be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the hydroperoxide of formula (IV) produced may be concentrated by distilling off the unreacted alkylbenzene of formula (II) prior to the cleavage step.

Optionally, oxidation of the alkylbenzene feedstock may also take place in the presence of a transition metal co-catalyst, for example, cobalt, manganese or copper. However, it is preferred that no transition metal co-catalyst is used, especially when the catalyst is a cyclic imide of formula III in which X represents a carbonyl (CO) group.

Oxidation is an exothermic reaction, and the heat of reaction is removed from the oxidation reaction mixture during the reaction. For example, heat is removed by vaporization of hydrocarbon, product and water, if water is present in the oxidation mixture, into the air passing through the reactor(s). If necessary, external heat exchangers can be used to cool the vaporized products and recirculate them to the oxidation reactor(s).

Hydroperoxide Cleavage

The oxidation product comprises a hydroperoxide of formula (IV), preferably, sec-butylbenzene hydroperoxide, that is separated from the reaction mixture by methods well known in the art, such as vacuum distillation, stripping, washing, condensing and decanting, which is then cleaved into phenol and a ketone of formula (I), preferably methyl ethyl ketone. Cleavage is preferably done in a cleavage reactor or reactor zone, operating, for example, as a plug flow reactor, a plug flow reactor with recycle or a continuous stirred tank reactor.

This cleavage reaction is effected by containing the hydroperoxide of formula (IV) in a liquid phase with a catalyst at a temperature of about 20° C. to about 150° C., such as about 40° C. to about 120° C., a pressure of about 50 kPa to about 2500 kPa, such as about 100 kPa to about 1000 kPa and a liquid hourly space velocity (LHSV) based on the hydroperoxide of about 0.1 $hr^{-1}$ to about 100 $hr^{-1}$, preferably about 1 $hr^{-1}$ to about 50 $hr^{-1}$. The hydroperoxide of formula (IV) is preferably diluted in an organic solvent inert to the cleavage reaction, such as the ketone of formula (I), phenol or the alkylbenzene of formula (II), to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid. Examples of suitable conditions for cleaving sec-butylbenzene hydroperoxide may be found for example in WO 2004/074227, the entire disclosure of which is incorporated herein by reference.

A suitable heterogeneous catalyst for use in the cleavage of the hydroperoxide of formula (IV) includes a smectite clay, such as an acidic montmorillonite silica-alumina clay, as described in U.S. Pat. No. 4,870,217, the entire disclosure of which is incorporated herein by reference.

The product of cleavage is then sent to a recovery zone, in which a phenol crude fraction and a ketone crude fraction are separated by known methods, each crude fraction being further purified by known methods to produce the desired phenol and ketone of formula (I). Further details of product purification methods may be found for example in WO 2004/074230, WO 2004/072009 and WO 2004/072008, the entire disclosures of which are incorporated herein by reference.

EXAMPLES

The following non-limiting examples are provided to illustrate the benefits of the invention.

Example 1

Oxidation of Cumene and Sec-butylbenzene (SBB) Without Catalyst

To a 250-ml round bottom flask fitted with a condenser, stirrer and an air sparger, was charged 100 g of sec-butylbenzene (99.9% sec-butylbenzene, available from TCI) or cumene (99.9% cumene, available from TCI). The flask was heated using a temperature-controlled heating mantle. The reaction temperature was 110° C. and the pressure was atmospheric. The air flow rate was maintained approximately at 220 cc/min. Every 45 minutes, a small aliquot of the reaction mixture was removed from the flask and analyzed by GC. The results are presented in FIG. 1, which shows that there was no conversion of SBB under these conditions, while cumene conversion was approximately 3.4% per hour under the same conditions.

Example 2

Effect of Temperature on SBB Oxidation Without Catalyst

Figure 2:
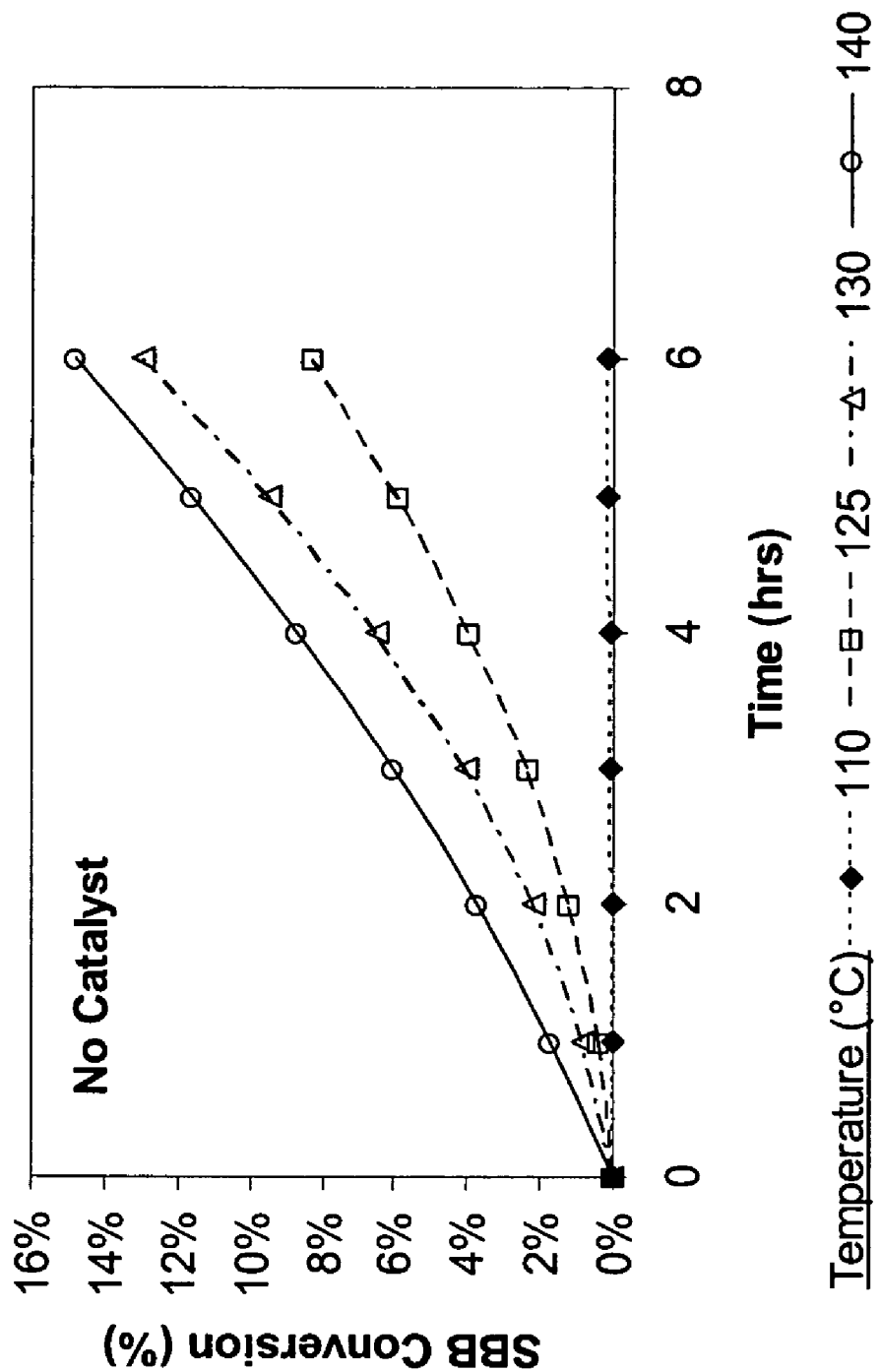
FIG. 2 shows SBB conversion during oxidation with air under atmospheric pressure at 110° C., 125° C., 130° C. and 140° C.
Figure 3:
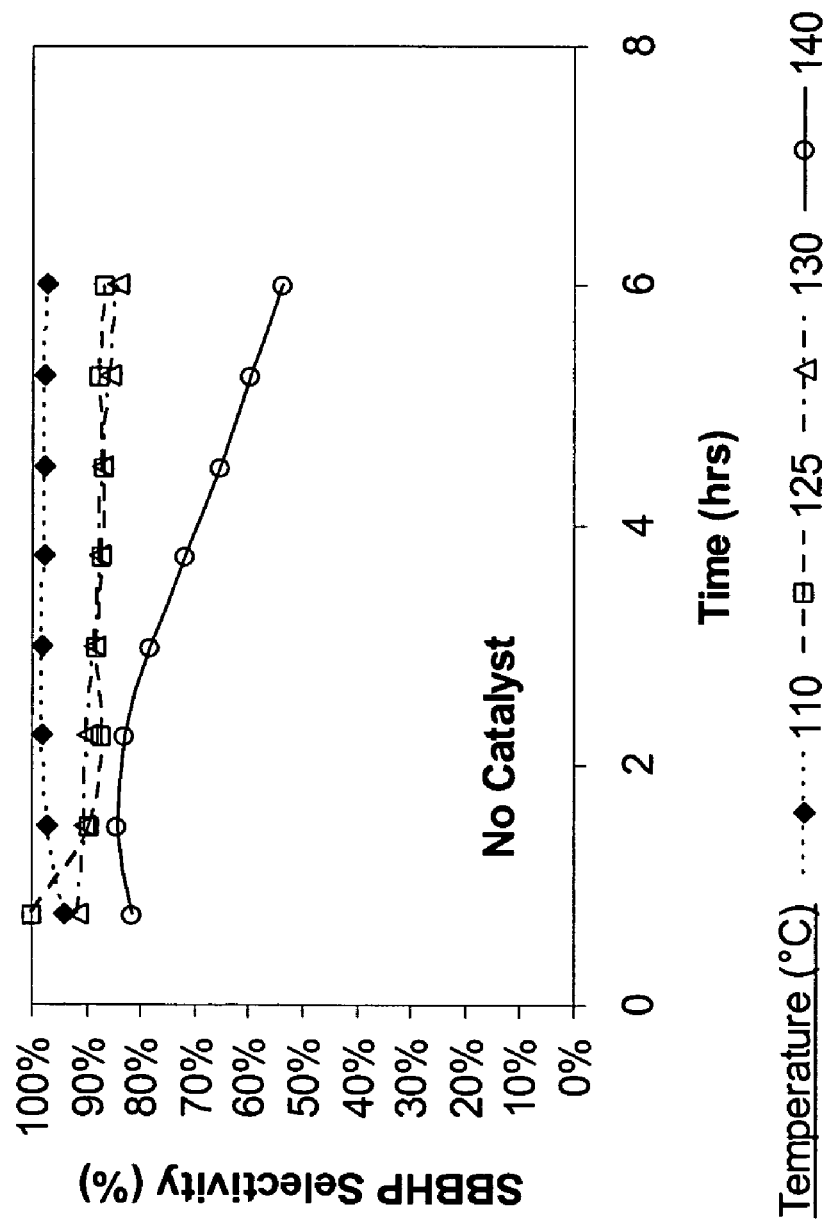
FIG. 3 shows selectivity to sec-butylbenzene hydroperoxide (SBBHP) during oxidation with air under atmospheric pressure at 110° C., 125° C., 130° C. and 140° C.

To a 250-ml round bottom flask fitted with a condenser, stirrer and an air sparger, was charged 100 g of sec-butylbenzene (available from TCI). The flask was heated using a temperature-controlled heating mantle. Different temperatures were evaluated at 110° C., 125° C., 130° C. and 140° C. The reaction pressure was atmospheric. The air flow rate was maintained approximately at 220 cc/min. Every 45 minutes, a small aliquot of the reaction mixture was removed from the flask and analyzed by GC. The results are shown in FIGS. 2 and 3, which show that SBB conversion takes place at temperatures higher than 110° C., but as the temperature gets higher, selectivity to sec-butylbenzene hydroperoxide (SBBHP) decreases.

Example 3

Effect of Temperature on SBB Oxidation—With Catalyst

Figure 4:
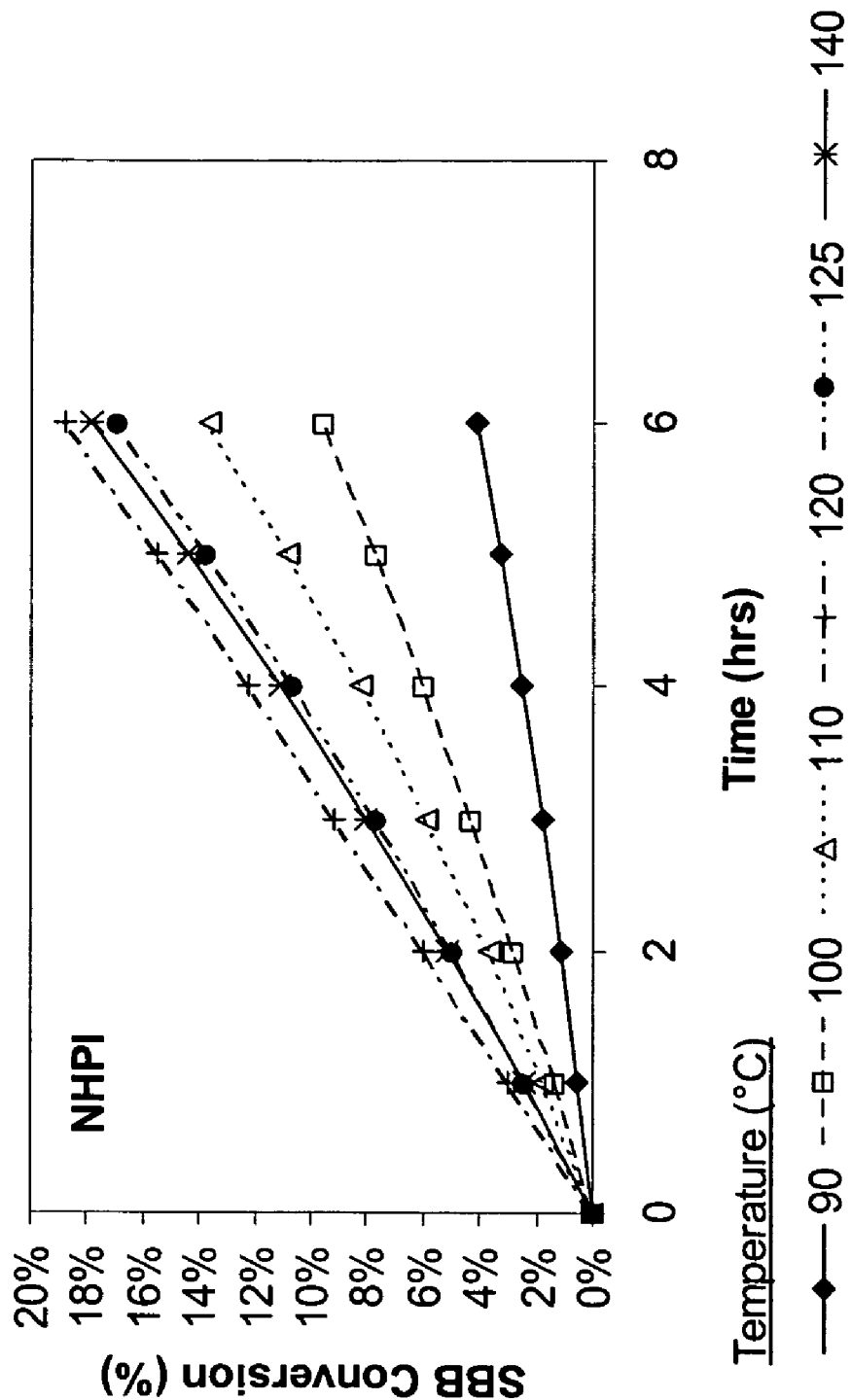
FIG. 4 shows SBB conversion during oxidation with air under atmospheric pressure, in the presence of NHPI, at 90° C., 100° C., 110° C., 120° C., 125° C. and 140° C.
Figure 5:
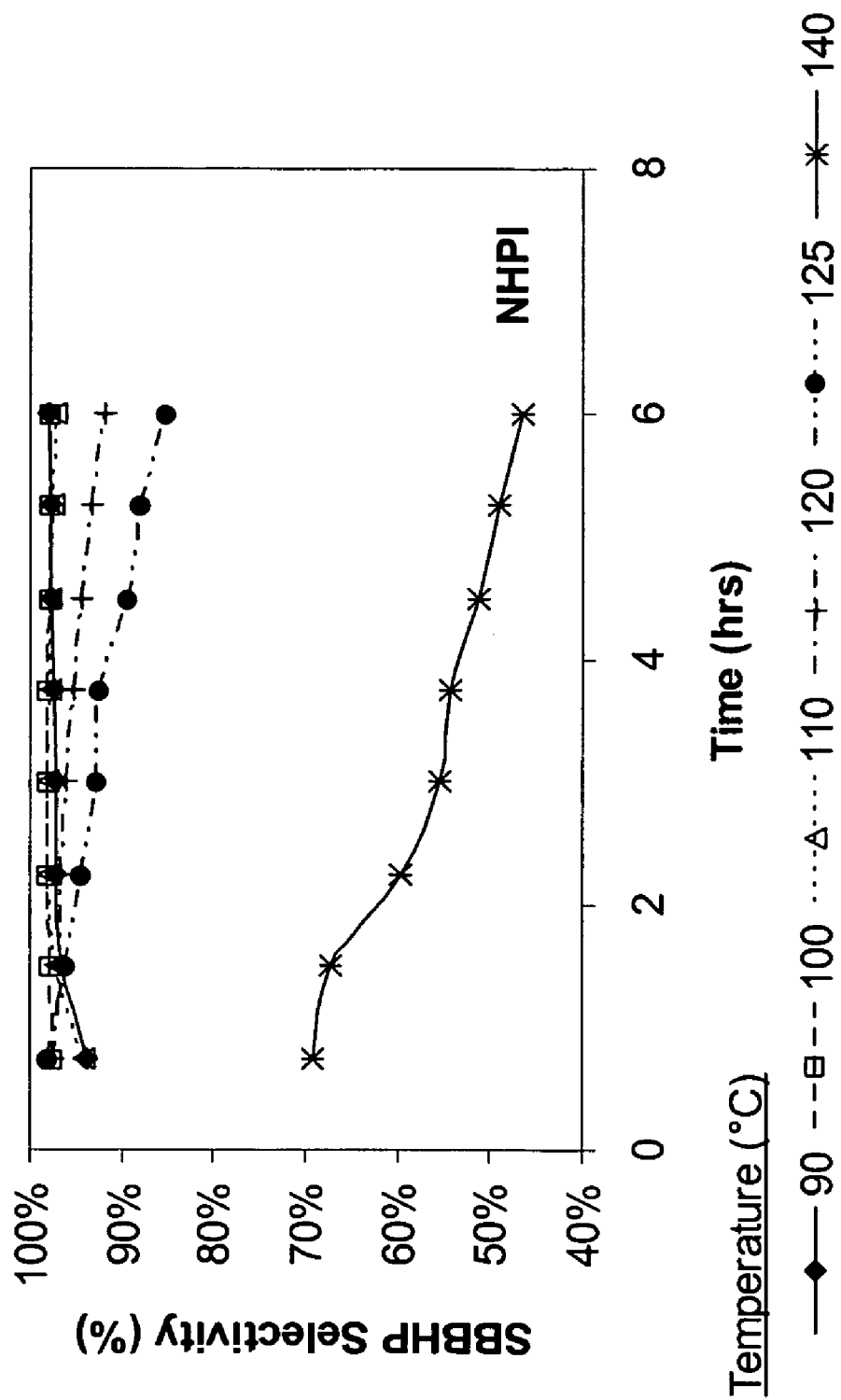
FIG. 5 shows selectivity to sec-butylbenzene hydroperoxide (SBBHP) during oxidation with air under atmospheric pressure, in the presence of NHPI, at 90° C., 100° C., 110° C., 120° C., 125° C. and 140° C.

To a 250-ml round bottom flask fitted with a condenser, stirrer and an air sparger, was charged 100 g of sec-butylbenzene (SBB, available from TCI) and 0.375 g N-hydroxyphthalimide (NHPI, available from Aldrich). The flask was heated using a temperature-controlled heating mantel. Different reaction temperatures were evaluated, at 90° C., 100° C., 110° C., 120° C., 125° C., 140° C. The reaction pressure was atmospheric. The air flow rate was maintained approximately at 220 cc/min. Every 45 minutes, a small aliquot of the reaction mixture was removed from the flask and analyzed by GC. The results are shown in FIGS. 4 and 5, which show that SBB conversion occurred at temperatures as low as 90° C. and proceeded with high selectivity to sec-butylbenzene hydroperoxide (SBBHP) at temperatures as high as 125° C.

Example 4

Effect of SBB Isomers on Sec-butylbenzene Oxidation—Without Catalyst

To a 250-ml round bottom flask fitted with a condenser, stirrer and an air sparger, was charged 100 g of sec-butylbenzene (SBB, available from TCI). The flask was heated using a temperature-controlled hearing mantle. Reaction temperature was 130° C. The reaction pressure was atmospheric. The air flow rate was maintained approximately at 220 cc/min. Every 45 minutes, a small aliquot of the reaction mixture was removed from the flask and analyzed by GC.

Figure 6:
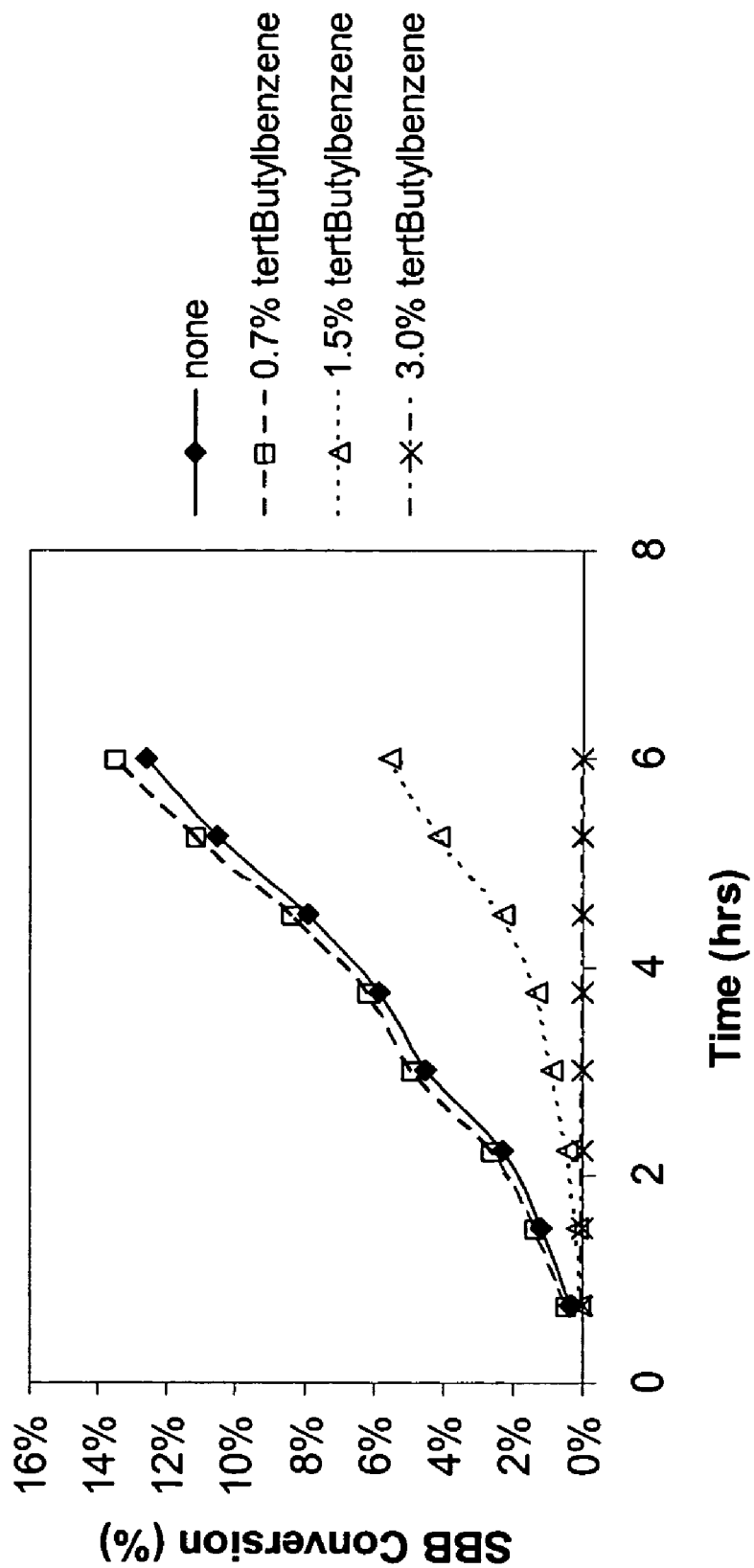
FIG. 6 shows SBB conversion during oxidation with air under atmospheric pressure at 130° C., in the absence of tert-butylbenzene, and in the presence of 0.7%, 1.5% and 3.0% tert-butylbenzene.
Figure 7:
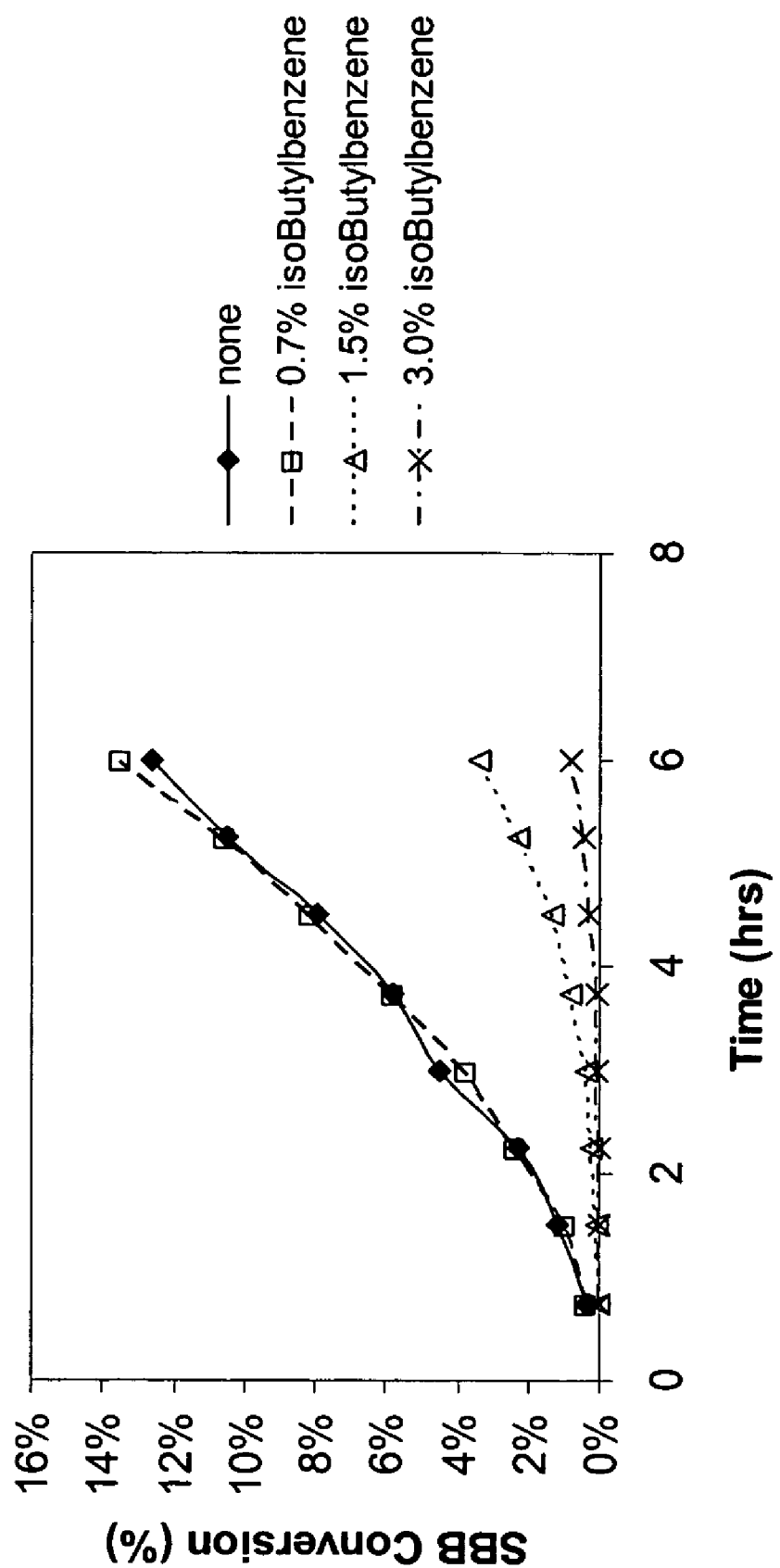
FIG. 7 shows SBB conversion during oxidation with air under atmospheric pressure at 130° C., in the absence of isobutylbenzene, and in the presence of 0.7%, 1.5% and 3.0% isobutylbenzene.

The procedure was repeated, except known amounts of tert-butylbenzene and iso-butylbenzene were added to the sec-butylbenzene feedstream. The results are shown in FIGS. 6 and 7, respectively, which show that, at concentrations about 0.7 wt %, sec-butylbenzene oxidation is significantly affected by the presence of tert-butylbenzene or iso-butylbenzene.

Example 5

Effect of SBB Isomers on Sec-butylbenzene Oxidation—With Catalyst

Figure 8A:
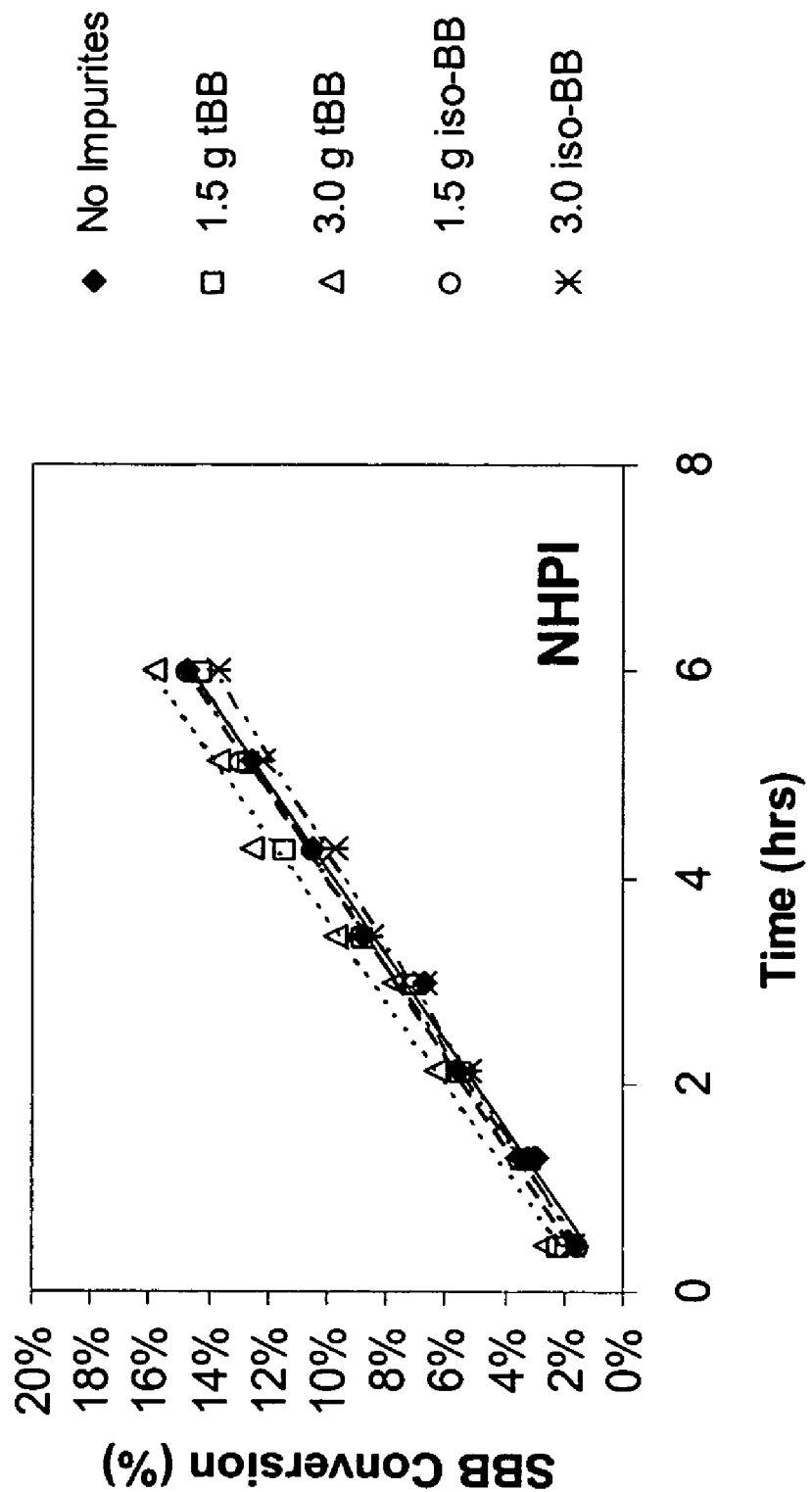
FIGS. 8a and 8b show SBB conversion during oxidation with air under atmospheric pressure, in the presence of NHPI at 115° C., in the absence of any structural isomers, and in the presence of structural isomer impurities.
Figure 8B:
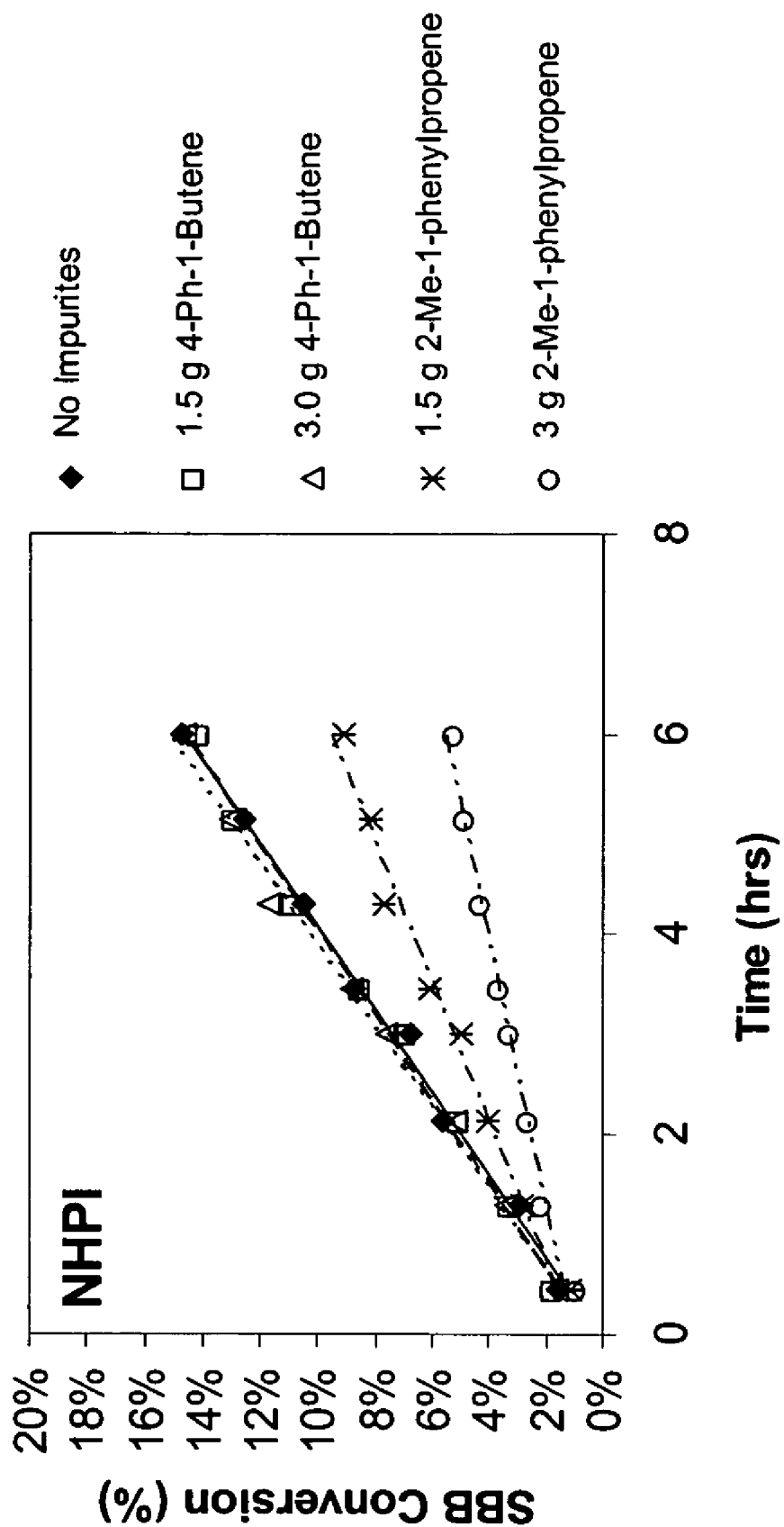

To a 250-ml round bottom flask fitted with a condenser, stirrer and an air sparger, was charged 100 g of sec-butylbenzene (SBB, available from TCI) and 0.375 g N-hydroxyphthalimide (NHPI, available from Aldrich). The flask was heated using a temperature-controlled heating mantel. Reaction temperature was 115° C. The reaction pressure was atmospheric. The air flow rate was maintained approximately at 220 cc/min. Every 45 minutes, a small aliquot of the reaction mixture was removed from the flask and analyzed by GC. The procedure was repeated, except known amounts of iso-butylbenzene, tert-butylbenzene, 4-phenyl-1-1butene and 2-methyl-1-phenylpropene were added to the sec-butylbenzene feedstream. The results are shown in FIG. 8, that shows that, even at concentrations as high as 3 wt %, sec-butylbenzene oxidation in the presence of NHPI is not affected by the presence of iso-butylbenzene, tert-butylbenzene or 4-phenyl-1-butene, and only moderately affected by the presence of 2-methyl-1-phenylpropene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing phenol and a ketone of general formula $R^1COCH_2R^2$ (I), in which $R^1$ and $R^2$ each independently represent an alkyl group having from 1 to 4 carbon atoms, said process comprising:
    (a) providing an alkylbenzene feedstock comprising
    (i) an alkylbenzene of general formula (II)

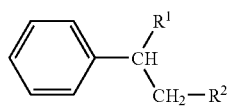
(II)

in which $R^1$ and $R^2$ have the same meaning as in formula (I) and
    (ii) at least one structural isomer of said alkylbenzene of formula (II) in an amount of at least 0.7% of the weight of alkylbenzene of formula (II),
    (b) submitting the alkylbenzene feedstock to oxidation conditions in the presence of oxygen and in the presence of a cyclic imide of formula (III):

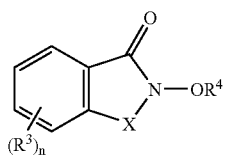
(III)

in which X represents a carbonyl (CO) group or a sulfonyl (SO$_2$) group, n is 0, 1, 2, 3 or 4, $R^3$ is one or several groups selected from a hydrogen atom, a halogen atom, an alkyl group, an alkoxy group, an amino group and $R^4$ is a hydrogen atom, an alkaline metal cation or an alkaline earth metal cation, or in the presence of N,N',N"-trihydroxyisocyanuric acid (THICA), to produce a product comprising a hydroperoxide of general formula (IV)

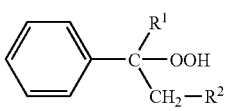
(IV)

in which $R^1$ and $R^2$ have the same meaning as in formula (I), and
    (c) converting the hydroperoxide of formula (IV) into phenol and a ketone of formula (I).

2. The process of claim 1, wherein oxidation takes place at a temperature of from 90° C. and 130° C., preferably at a temperature of from 100° C. to 125° C., more preferably at a temperature of from 105° C. to 120° C.

3. The process of claim 1, wherein oxidation takes place at a pressure of from about 50 kPa to 1000 kPa.

4. The process of claim 3, wherein oxidation takes place at a pressure of from 50 kPa to 500 kPa.

5. The process of claim 3, wherein oxidation takes place at a pressure of from 90 kPa to 150 kPa.

6. The process of claim 1, wherein the structural isomers of the alkylbenzene of formula (II) are selected from the group consisting of alkylbenzene of formula

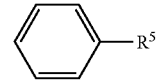
(V)

in which $R^5$ is an alkyl or alkene group having the same number of carbon atoms, but a different carbon chain structure, as benzene substituent $R^1$—CH—CH$_2$—$R^2$ in formula (II).

7. The process of claim 1, wherein $R^1$ and $R^2$ both represent a methyl group.

8. The process of claim 1, wherein the structural isomers are selected from the group consisting of n-butylbenzene, isobutylbenzene, tertbutylbenzene, 4-phenyl-1-butene, 2-methyl-1-phenylpropene, and mixtures thereof.

9. The process of claim 1, wherein the alkylbenzene feedstock contains structural isomers of the alkylbenzene of formula (II) in an amount of at least 1.0% of the weight of the alkylbenzene of formula (II).

10. The process of claim 1, wherein the alkylbenzene feedstock contains structural isomers of the alkylbenzene of formula (II) in an amount of at least 1.5% of the weight of the alkylbenzene of formula (II).

11. The process of claim 1, wherein the alkylbenzene feedstock contains structural isomers of the alkylbenzene of formula (II) in an amount that is no greater than 3% of the weight of alkylbenzene of formula (II).

12. The process of claim 1, wherein the alkylbenzene of formula (II) represents at least 80 wt % of the alkylbenzene feedstock.

13. The process of claim 1, wherein the alkylbenzene of formula (II) represents at least 90 wt % of the alkylbenzene feedstock.

14. The process of claim 1, wherein the alkylbenzene of formula (II) represents at least 95 wt % of the alkylbenzene feedstock.

15. The process of claim 1, wherein the alkylbenzene of formula (II) represents at least 97 wt % of the alkylbenzene feedstock.

16. The process of claim 1, wherein the alkylbenzene feedstock contains structural isomers of the alkylbenzene of formula (II) in an amount that is at least 2.0% of the weight of alkylbenzene of formula (II).

17. The process of claim 1, wherein the alkylbenzene feedstock contains structural isomers of the alkylbenzene of formula (II) in an amount that is at least 2.5% of the weight of alkylbenzene of formula (II).

18. The process of claim 1, wherein the cyclic imide of formula (III) is selected from the group consisting of N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxysaccharin, and mixtures thereof.

19. The process of claim 1, wherein the cyclic imide of formula (III) is N-hydroxyphthalimide.

20. The process of claim 1, wherein the cyclic imide of formula (III) or THICA is present in amount of from 0.0001 mol % to 15 mol % relative to the amount of alkylbenzene of formula (II).

21. The process of claim 1, wherein the cyclic imide of formula (III) or THICA is present in amount of from 0.001 mol % to 10 mol % relative to the amount of alkylbenzene of formula (II).

22. The process of claim 1, wherein the cyclic imide of formula (III) or THICA is present in an amount of no more than 5 mol % relative to the amount of alkylbenzene of formula (II).

23. The process of claim 1, wherein the cyclic imide of formula (III) or THICA is present in an amount of no more than 4 mol % relative to the amount of alkylbenzene of formula (II).

24. The process of claim 1, wherein the cyclic imide of formula (III) or THICA has been deposited or fixed chemically on a support.

25. The process of claim 24, wherein the support is silica, alumina, a zeolite, a polymer or a mixture thereof.

26. The process of claim 1, wherein step (b) takes place in the presence of a transition metal.

27. The process of claim 26, wherein the transition metal is selected from cobalt, manganese, copper and mixtures thereof.

28. The process of claim 1, wherein step (c) is conducted in the presence of a catalyst.

29. The process of claim 28, wherein the catalyst is selected from the group consisting of sulfuric acid, perchloric acid, phosphoric acid, hydrochloric acid, p-toluenesulfonic acid, ferric chloride, boron trifluoride, sulfur dioxide and sulfur trioxide.

30. The process of claim 28, wherein the catalyst comprises s smectite clay.

31. The process of claim 1, wherein step (c) is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

32. The process of claim 1, wherein step (b) is performed in the presence of N,N',N"-trihydroxyisocyanuric acid (THICA).

33. The process of claim 1, wherein step (b) is conducted in a catalytic distillation unit.

34. The process of claim 1, wherein the amount of structural isomer present in the alkylbenzene feedstock does not exceed 10% of the weight of alkylbenzene of formula (II).

35. The process of claim 1, wherein the amount of structural isomer present in the alkylbenzene feedstock does not exceed 5% of the weight of alkylbenzene of formula (II).

36. The process of claim 1, wherein the amount of structural isomer present in the alkylbenzene feedstock does not exceed 4% of the weight of alkylbenzene of formula (II).

* * * * *